(12) United States Patent
Renlund et al.

(10) Patent No.: US 10,254,237 B2
(45) Date of Patent: Apr. 9, 2019

(54) MICROFABRICATED SENSOR AND A METHOD OF DETECTING A COMPONENT IN BODILY FLUID

(71) Applicant: ASCILION AB, Kista (SE)

(72) Inventors: Markus Renlund, Akersberga (SE); Dragos Stefan Dancila, Uppsala (SE)

(73) Assignee: ASCILION AB, Kista (SE)

( * ) Notice: Subject to any disclaimer, the term of this patent is extended or adjusted under 35 U.S.C. 154(b) by 97 days.

(21) Appl. No.: 15/316,957

(22) PCT Filed: Jun. 7, 2014

(86) PCT No.: PCT/SE2014/000075
§ 371 (c)(1),
(2) Date: Dec. 7, 2016

(87) PCT Pub. No.: WO2015/187066
PCT Pub. Date: Dec. 10, 2015

(65) Prior Publication Data
US 2017/0115236 A1    Apr. 27, 2017

(51) Int. Cl.
*G01R 27/04* (2006.01)
*G01N 22/00* (2006.01)
(Continued)

(52) U.S. Cl.
CPC .......... *G01N 22/00* (2013.01); *A61B 5/0507* (2013.01); *A61B 5/14514* (2013.01);
(Continued)

(58) Field of Classification Search
CPC ...... G01N 22/00; G01N 33/487; G01N 33/50; G01N 33/5002; G01N 2021/0346;
(Continued)

(56) References Cited

U.S. PATENT DOCUMENTS

| 4,673,894 A | 6/1987 | Rogers |
| 4,912,982 A | 4/1990 | Yuki |

(Continued)

FOREIGN PATENT DOCUMENTS

| EP | 0511651 A2 | | 11/1992 |
| WO | WO 00/43759 | * | 1/2000 |
| WO | 2005/060621 A2 | | 7/2005 |

OTHER PUBLICATIONS

John L. Smith, "The Pursuit of Noninvasive Glucose: Hunting the Deceitful Turkey", Second edition 2011 (fourth edition: revised and expanded 2015), USA.

(Continued)

*Primary Examiner* — Thang X Le
(74) *Attorney, Agent, or Firm* — Young & Thompson

(57) ABSTRACT

A microfabricated sensor (1) for detecting a component in bodily fluid, includes: an inlet (2) for receiving a sample of bodily fluid, a fluid cavity (6) connected to the inlet for receiving the sample of bodily fluid from the inlet, and an RF resonant cavity (13), delimited by walls (14). At least one of the walls forms a separating wall (15), separating the fluid cavity from the RF resonant cavity, wherein the separating wall is configured such that the dielectric properties of the bodily fluid in the fluid cavity provide an influence on the electromagnetic properties of the RF resonant cavity.

21 Claims, 8 Drawing Sheets

(51) Int. Cl.
*G01N 33/487* (2006.01)
*A61B 5/00* (2006.01)
*A61B 5/05* (2006.01)
*A61B 5/145* (2006.01)
*A61B 5/15* (2006.01)
*A61B 5/157* (2006.01)

(52) U.S. Cl.
CPC ........ *A61B 5/157* (2013.01); *A61B 5/150022* (2013.01); *A61B 5/150396* (2013.01); *A61B 5/150984* (2013.01); *A61B 5/685* (2013.01); *G01N 33/487* (2013.01); *A61B 5/14532* (2013.01); *A61B 2562/028* (2013.01); *A61B 2562/12* (2013.01)

(58) Field of Classification Search
CPC ... G01N 2015/0073; G01N 2015/0288; G01N 2015/0294; G01N 2015/0681; G01N 35/1079; G01N 2035/00237; G01N 2035/00554; G01N 2291/02466; G01N 2291/0256; G01N 2291/0421
See application file for complete search history.

(56) References Cited

U.S. PATENT DOCUMENTS

| | | | | |
|---|---|---|---|---|
| 5,260,665 | A * | 11/1993 | Goldberg | G01N 22/00 324/636 |
| 5,514,253 | A * | 5/1996 | Davis | G01N 27/404 204/403.13 |
| 5,674,742 | A * | 10/1997 | Northrup | B01F 11/0266 417/322 |
| 5,951,836 | A | 9/1999 | McAleer et al. | |
| 6,030,827 | A * | 2/2000 | Davis | C12Q 1/002 435/287.1 |
| 7,753,888 | B2 | 7/2010 | Mukerjee et al. | |
| 2003/0199081 | A1 * | 10/2003 | Wilding | B01D 61/18 435/287.2 |
| 2007/0213638 | A1 * | 9/2007 | Herbrechtsmeier | A61B 5/15186 600/583 |
| 2009/0189064 | A1 * | 7/2009 | Miller | G01N 27/624 250/282 |
| 2015/0313527 | A1 * | 11/2015 | Renlund | A61B 5/14532 600/347 |

OTHER PUBLICATIONS

Suresh et al. "Comparison of glucose concentration in interstitial fluid, and capillary and venous blood during rapid changes in blood glucose levels", vol. 3, No. 3, 2001, Diabetes Technology and Therepeutics, Phoenix, Arizona.

R.E. Collin, "Foundations for microwave engineering", McGraw-Hill, New York, 1966 (2nd edition 2001, and IEEE Press classic reissue), Hoboken, New Jersey.

Kim et al: "In vitro monitoring of goat-blood glycemia with a microwave biosensor", Current Applied Physics, vol. 14, No. 4, Jan. 31, 2014 (Jan. 31, 2014), pp. 563-569, Texas, USA, XP028841468.

Gianluca Gennarelli et al: "A Microwave Resonant Sensor for Concentration Measurements of Liquid Solutions", IEEE Sensors Journal, IEEE Service Center, New York, NY, US, vol. 13, No. 5, May 2013 (May 2013), pp. 1857-1864, XP011499518, ISSN: 1530-437X.

Yun Fan et al: "Testing glucose concentration in aqueous solution based on microwave cavity perturbation technique", Biomedical Engineering and Informatics (BMEI), 2010 3RD International Conference on, IEEE, Piscataway, NJ, USA, Oct. 16, 2010 (Oct. 16, 2010), pp. 1046-1049, XP031804229.

International Search Report dated Dec. 2, 2014, in corresponding PCT application.

* cited by examiner (a)

(b)

(a)

(b)

(c)

(d)

(e)

(f)

(g)

MICROFABRICATED SENSOR AND A METHOD OF DETECTING A COMPONENT IN BODILY FLUID

TECHNICAL FIELD

The present invention relates to a microfabricated sensor and a method of detecting or sensing the level of a component in bodily fluid.

BACKGROUND ART

There are numerous applications where there is a need of detecting a component or sensing a level of a component in bodily fluids. These may be e.g. to diagnose an illness, adjusting a medication or detecting undesired or illegal substances in the body of a person.

As one example, glucose monitoring is part of an everyday life, especially for people with diabetes. To accommodate normal life, diabetic individuals need to accurately and frequently measure the glucose level in the body, preferably in a small amount of bodily fluid. The most common method to determine the blood glucose level is to use disposable glucose test strips and a glucose meter, see U.S. Pat. No. 5,951,836. To extract blood, a lancet pricks the finger and a drop of blood is placed on the strip. The main drawback with the glucose test strips is the pain from the extraction of blood using the lancet as well as the skin damage.

Other methods to measure the glucose level have been suggested in the prior art. The main goal is to develop a non-invasive method (see "The Pursuit of Noninvasive Glucose: Hunting the Deceitful Turkey", John L. Smith, Second edition 2011). Measurement techniques range from spectroscopic, optical, light scattering, breath and transdermal techniques. Techniques fail primarily due to difficulties to obtain an accurate glucose measurement. It has however been shown that the glucose level in interstitial fluid (ISF) correlates well to the blood glucose level (Suresh et al. "Comparison of glucose concentration in interstitial fluid, and capillary and venous blood during rapid changes in blood glucose levels", Vol 3, No 3, 2001, Diabetes Technology and Therepeutics).

The use of microfabrication to reduce the size of needles to minimize discomfort is a rapidly developing arena of investigation for the transcutaneous delivery of drugs. Such microneedles have been developed for extracting ISF transdermal, see U.S. Pat. No. 7,753,888.

SUMMARY OF INVENTION

An objective of the present invention is to provide a sensor for rapid and accurate detection of a component in bodily fluid.

Hence the present disclosure relates to a microfabricated sensor for detecting a component in bodily fluid. The sensor comprises an inlet means for receiving a sample of bodily fluid and a fluid cavity connected to the inlet means for receiving the sample of bodily fluid from the inlet means. The sensor further comprises a microwave resonator as an RF resonant cavity. A microwave resonator is an electromagnetic circuit that confines electromagnetic fields in a closed (or largely closed) metal structure. The structure is either hollow or filled with dielectric material. It is characterized by one or several resonant frequencies. The RF resonant cavity is delimited by walls, and wherein at least one of the walls forms further a separating wall, separating the fluid cavity from the RF resonant cavity. The separating wall is configured such that the dielectric properties of the bodily fluid in the fluid cavity provide an influence on the electromagnetic properties of the RF resonant cavity.

Thereby a sensor is provided which provides for a rapid and accurate detection of a component in bodily fluid by means of utilizing the perturbation of one or several of the RF cavity resonance modes. The resonant frequency associated with the RF cavity is a function of the cavity's dimensions and of any dielectric material (e.g. a gas, liquid or solid material) introduced in the RF cavity or in close proximity to the cavity. The coupling to a dielectric material outside the RF cavity, could be realized by capacitive or inductive coupling.

The separating wall may comprise a membrane. Thus the RF resonant cavity and the fluid cavity may be arranged in close vicinity to each other to enable a good coupling of the properties of fluid in the fluid cavity to the electromagnetic properties of the RF resonant cavity.

The walls of the RF resonant cavity may be at least partly metallized, but an RF coupling region may be provided at the separating wall, such that to couple the RF resonant cavity to the fluid cavity. The RF coupling region may be a non-conducting and/or a non-metallized area of the separating wall. Thereby the RF resonant cavity may be electromagnetically coupled to any body fluid collected in the fluid cavity.

The RF resonant cavity may be dimensioned and designed in such way that the coupling level and thereby sensitivity to components within the bodily fluid is optimized for given dielectric losses within the fluid in question. When dielectric losses are too high, the coupling to the bodily fluid is reduced, as a consequence sensitivity decreases.

The fluid cavity may comprise a portion extending into the RF resonant cavity, and the separating wall may comprise a wall of a dielectric material delimiting the portion of the fluid cavity protruding into the RF resonant cavity.

Thereby the dielectric properties of bodily fluid in a portion of the fluid cavity may be determined. This also enables other modes of electromagnetic interaction between the RF resonant cavity and the fluid cavity.

The RF resonant cavity may be formed as a cuboid volume, having a width, a length and a height, or a cylindrical volume having a height and a diameter.

The RF resonant cavity may comprise a tuning post or a plurality of tuning posts. The tuning post may be formed with both dielectric or metallized, conducting walls.

Thereby the resonance frequency of the RF resonant cavity may be tuned. This may be used to lower the resonance frequency of the RF resonant cavity in order to miniaturize the cavity. By providing a tuning post or a plurality of tuning posts in the RF resonant cavity, a cavity of smaller dimensions, and thus a sensor having a smaller footprint may obtained. This is very advantageous for batch microfabricated devices, since the number of sensors fabricated in a batch may be increased, decreasing the cost of each sensor.

The tuning post may be a cuboid, a cube or a cylinder, thus having a width, a length and a height. The tuning post may be centrally located in the RF resonant cavity, or at a wall of the cavity opposite the separating wall. The lateral dimensions of the tuning post may have a length and width, typically about 20-70%, or about 60% of the RF resonant cavity's lateral dimensions.

The tuning post or plurality of tuning posts may be configured to provide a gap in the RF resonant cavity, in the vicinity of the separating wall. Thus the height of the tuning post may be selected relative to the height of the RF resonant cavity in order to tune the resonant behavior of the cavity.

The tuning post may be dimensioned to provide a gap (a distance between one side of the tuning post and the RF resonant cavity) which is 1-10% of the height of the RF resonant cavity, typically 2% of the height of the RF resonant cavity. A smaller gap may enable a higher degree of miniaturization of the RF resonant cavity but a decrease of the Q factor. The Q-factor is the ratio between the maximum energy stored and the dissipated energy in the resonator, evaluated at the resonance frequency, during one period.

The portion of the fluid cavity extending into the RF resonant cavity may extend over the gap within the RF resonant cavity. Thereby fluid in the portion may provide an influence on the resonance of the RF resonant cavity.

A dimension of the fluid cavity may be 100 µm or more, preferably 200 µm or more.

The sensor may comprise a fluid exit port connected to the fluid cavity for drainage of fluid from the fluid cavity. Thereby bodily fluid may be extracted and transported by means of capillary suction in the sensor.

The fluid exit port may extend through the tuning post.

Electromagnetic (RF) energy may be introduced at one end of the RF resonant cavity and removed at the same end by capacitive or inductive coupling, or electromagnetic (RF) energy may be introduced at one end of the resonant cavity and removed at another end of the resonant cavity by capacitive or inductive coupling. This may be done e.g. through one or more coupling slots arranged in the resonant cavity.

The sensor may be configured in such way that the RF cavity is sealed off from the fluid cavity. Thereby bodily fluid in the fluid cavity may be capacitively or inductively coupled to the RF resonant cavity, but separated from the RF resonant cavity.

The inlet means may comprise at least one hollow microneedle for extraction of a sample of bodily fluid, preferably a plurality of hollow microneedles, more preferably 10 to 100 microneedles. Thereby bodily fluid, such as interstitial fluid (ISF) or blood may be extracted and introduced into the sensor with minimal discomfort for the patient.

The at least one microneedle may comprise a capillary bore, e.g. a single capillary bore. Thereby bodily fluid may be extracted by means of capillary suction through the microneedle, fluid cavity and fluid exit port. Alternatively, or in addition, a suction force may be applied to the fluid cavity or the fluid exit port.

The at least one microneedle may be provided with a cap at a distal end for shielding the capillary bore from clogging, whereby at least one opening to the capillary bore is provided in a lateral direction of the microneedle, perpendicular to the axial or longitudinal extension of the microneedle.

A plurality of openings may be provided in a lateral direction, around a circumference of the microneedle. The at least one opening may be provided about midways along a longitudinal extension of the microneedle. Thereby the extraction of bodily fluid is facilitated and the risk for clogging is further reduced.

The capillary bore of the at least one microneedle may be provided with a hydrophilic surface. Thereby capillary flow of bodily fluid may be assisted.

The microneedle may comprise a plurality of cutting elements extending along a longitudinal direction of the microneedle. Thereby the skin may be cut and opened to facilitate extraction of bodily fluid.

The at least one microneedle may have a length of 200-1000 µm, preferably 400-900 µm, more preferably 500-600 µm, and an outer diameter of 50-200 µm, preferably 80-150 µm. Thereby the microneedle has dimensions suitable for penetration of the skin and extraction of bodily fluid.

The at least one microneedle may be at least partly surrounded by a frame structure dimensioned to support the tip of a finger. Thereby the skin of the tip of the finger may be supported and tensioned to facilitate penetration of the at least one microneedle into the skin.

The frame structure dimensioned to support the tip of a finger is a ring shaped structure protruding along the longitudinal direction of the at least one microneedle, and preferably having a diameter of 1-5 mm, more preferably 2-3 mm.

The sensor may be configured for detecting a level of glucose in bodily fluid, i.e. a glucose sensor. Thereby a sensor for rapid and accurate detection of the level of glucose in bodily fluid may be provided.

The disclosure further relates to a method of detecting a component in bodily fluid of a patient comprising providing a sensor as disclosed herein,
providing a sample of bodily fluid at the inlet means,
receiving the fluid sample in the fluid cavity,
performing an RF measurement by exciting the RF resonant cavity with an RF signal and detecting an RF response, and detecting the component based on the performed RF measurement.

The detection of the component may be based on an oscillator circuit using a one or two port coupling structure into the RF cavity resonator. The RF measurement may be based upon a filter design and a 1 or 2 port cavity resonator.

The RF measurement may be based upon a resonator readout and a 1 or 2 port measurement.

The step of detecting the component may comprise determining the level of the component based on the performed RF measurement.

The bodily fluid may be blood and/or interstitial fluid (ISF).

The component may be glucose.

The RF measurement may be performed at frequencies in the range of 2-50 GHz, more preferably in the range of 8-20 GHz most preferably in the range of 16-18 GHz for miniaturization of the device.

BRIEF DESCRIPTION OF DRAWINGS

The invention is now described, by way of example, with reference to the accompanying drawings, in which.

DESCRIPTION OF EMBODIMENTS

In the following, a detailed description of various embodiments of microfabricated sensors and a method of detecting or sensing the level of a component in bodily fluid is disclosed.

Figure 1:
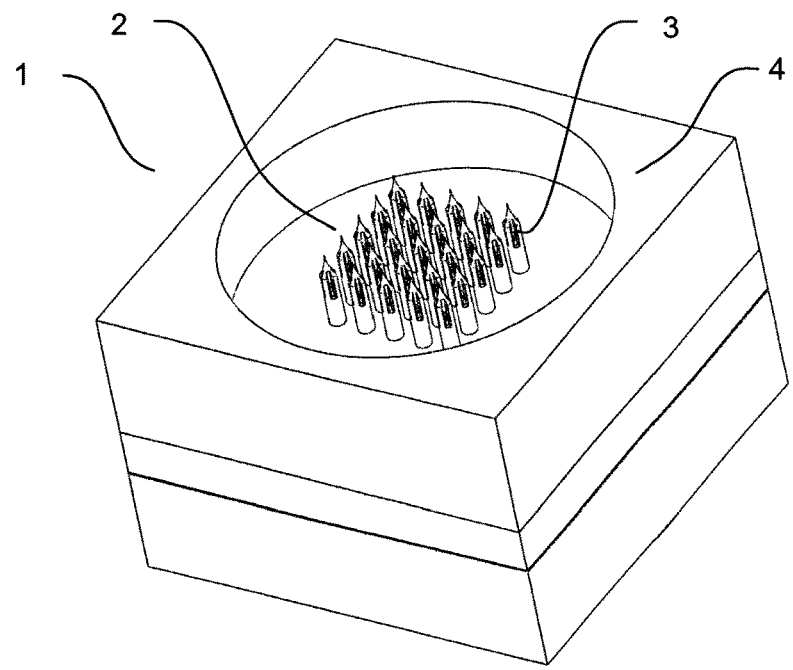
FIG. 1 shows a microfabricated sensor according to a first example, in perspective view.

In FIG. 1 a first example of a microfabricated sensor 1 for detecting a component in bodily fluid is shown. The sensor is provided with an inlet means 2 for receiving a sample of bodily fluid, in the form of a plurality of hollow microneedles 3. The hollow microneedles are provided for minimal invasive extraction of a sample of bodily fluid from a user. The term minimally invasive implies that there is minimal damage to biological tissues at the point of entrance of the microneedles, thus reducing the discomfort of the patient. The microneedles are arranged in an array of 5×5 needles, i.e. in this case 25 microneedles.

A ring shaped frame structure 4 surrounds the microneedles. The inner diameter of the ring shaped structure is in the range of 1-5 mm, typically 2-3 mm, and is thus dimensioned to support the tip of a finger. The tips of the microneedles are protected by the upper surface of the ring shaped frame structure, such that they do not protrude beyond this upper surface. Thus the needles are protected from breakage during fabrication and handling of the sensor, and the sensor may be sealed by a protective film during fabrication and handling. The ring shaped structure has the effect that the skin of the tip of a finger pressed towards the microneedles may be brought into tension, thereby facilitating the penetration of the microneedles through the skin.

Figure 2:
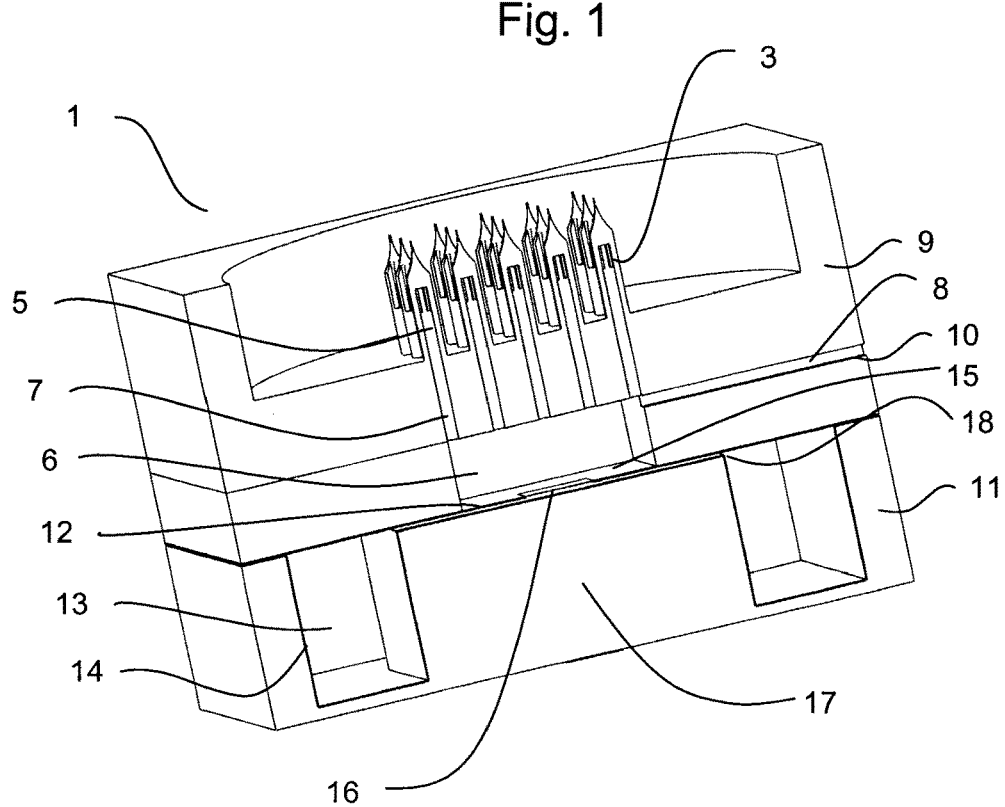
FIG. 2 shows the microfabricated sensor according to the first example, in a cross-sectional view.

In FIG. 2, the sensor 1 shown in FIG. 1 is shown in cross-section. The microneedles 3 each comprises a single capillary bore 5, and the sensor further comprises a fluid cavity 6 connected to the microneedles for receiving a sample of bodily fluid extracted by the microneedles. Each microneedle is connected to the fluid cavity via bore holes 7 for capillary fluid transport. The fluid cavity is open to the ambient through a fluid exit port 8 to enable capillary suction of the bodily fluid. The sensor is microfabricated out of a needle wafer 9, a fluid cavity wafer 10 and a RF cavity wafer 11, which are stacked together.

The bottom of the fluid cavity 6, i.e. the side of the fluid cavity facing the RF cavity wafer 11, is formed by a membrane 12 having a thickness much smaller than the lateral extension of the membrane. The thickness of the membrane may be in the range of 1-2 µm. The membrane is formed by a dielectric material, e.g. silicon.

The sensor further comprises a RF resonant cavity 13 formed in the RF cavity wafer 11. The RF resonant cavity is delimited by walls 14 which are at least partly metalized to confine the electromagnetic fields. The RF resonant cavity faces the membrane of the fluid cavity, whereby the membrane forms a portion of a wall delimiting the RF cavity. The membrane thus forms a separating wall 15, separating the fluid cavity from the RF resonant cavity.

The walls 14 of the RF cavity are made electrically conducting. However at the membrane 12, a portion 16 of the wall defined by the membrane is left with an opening in the metallization. The material of the membrane is itself a dielectric material. Thereby the separating wall is configured such that the dielectric properties of the bodily fluid in the fluid cavity provide an influence on the electromagnetic properties of the RF resonant cavity. Further, one or more coupling slots configured for coupling RF energy into and out from the resonant cavity are provided as openings, or provided without any metallization.

The RF resonant cavity 13 is formed as a cuboid cavity. The resonant cavity has outer dimensions having a length in the range of 1-3 mm, preferably 2-2.5 mm or about 2.4 mm, a width in the range of 1-3 mm, preferably 2-2.5 mm or about 2.4 mm and a height in the range of 0.5-1 mm, preferably 0.6-0.8 mm or about 650 µm. In the RF resonant cavity, protruding from the side of the cavity opposite of the separating wall, a tuning post 17 having a cuboid shape protrudes into the cavity. The tuning post has a function of tuning the resonant behavior of the RF resonant cavity. The walls of the tuning post are electrically conducting by a metallization layer or by other means.

A tuning post positioned in the RF resonant cavity predominantly perturbs the electric or magnetic field distribution within the cavity. The tuning post thereby reduces or increases the resonance frequency of the cavity resonator. The size and position of the tuning post (width, length and height) determines the shift in resonance frequency. Hence the size of the RF resonant cavity can be miniaturized for a given resonance frequency by choice of geometry and location of the tuning post. In the example shown, the tuning post has a width×length×height of 1440 µm×1440 µm×637 µm.

Typically for the fundamental mode of resonance, i.e. the TE101 mode of a cuboid cavity, the dimensions, geometry and location of the at least one tuning post 17 are calculated with respect to the electromagnetic fields present in the RF resonant cavity. Tuning posts of such dimension and placement may in such way generate a change in resonance frequency of the fundamental mode or other modes of resonance. By placing the at least one tuning post in the center of the cavity, the resonance frequency of the fundamental mode is minimized and conversely the resonance frequency of the fundamental mode is increased by placing the at least one tuning post at a side of the RF resonant cavity. Hence the resonance frequency of the fundamental mode may be tailored by proper design and placement of the at least one tuning post.

By providing a tuning post 17 in the center of the RF resonant cavity 13 as shown in FIG. 2, the dimensions of the resonant cavity may be minimized while maintaining a certain fundamental resonance frequency of the cavity. This is important in order to minimize the dimensions of the sensor. By minimizing the footprint of the sensor, a greater number of sensors may be fabricated in a single batch of sensors, thereby reducing the cost of each sensor.

The shift in resonance frequency may be calculated by applying the perturbation theory (R. E. Collin, Foundations for microwave engineering, McGraw-Hill, New York, 1966). The field distribution is used to compute the electric energy, $W_e$ and magnetic energy, $W_m$ stored in the initial cavity volume and $\Delta W_e$ and $\Delta W_m$, the electric and magnetic energy stored in the corresponding perturbed volume, respectively evaluated as follows:

$$W_e = \frac{\varepsilon}{4}\int_v |\vec{E}|^2 dv$$

$$W_m = \frac{\mu}{4}\int_v |\vec{H}|^2 dv$$

Where the volume of integration is v=a×d×b for $W_e$ and $W_m$ and is v=W×L×Hbox for $\Delta W_e$ and $\Delta W_m$. Additionally, $E_0$ and $H_0$ are the unperturbed electric and magnetic fields, respectively. The frequency shift is evaluated as the fraction of the difference between the magnetic energy and electric energy stored in the perturbed volume to the total energy stored in the cavity:

$$\frac{f - f_0}{f_0} \cong \frac{\Delta W_m - \Delta W_e}{W_m + W_e}$$

where f and $f_0$ are the perturbed and unperturbed resonance frequency, respectively.

The larger the lateral dimensions of the tuning post, the larger the equivalent stored energy in the volume of the tuning post. The stored electrical energy is higher than the magnetic stored energy, as the post is centrally located in the cavity resonator, where the electric field is dominant for the TE101 mode. In this specific case, the result of the post perturbation is a decrease of the resonance frequency.

The tuning post is dimensioned to provide a gap 18 between the tuning post 17 and the membrane 12. The gap in the example shown is 13 µm wide. The dimensions of the tuning post and the gap are carefully selected to tune the fundamental resonance frequency of the chamber and to provide an efficient coupling of the resonant cavity to the fluid cavity.

Figure 3:
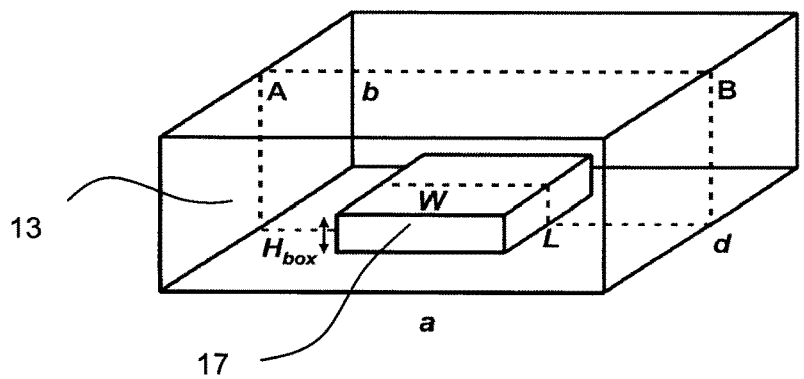
FIG. 3 shows the microfabricated sensor according to the first example, in an exploded view.
Figure 3:
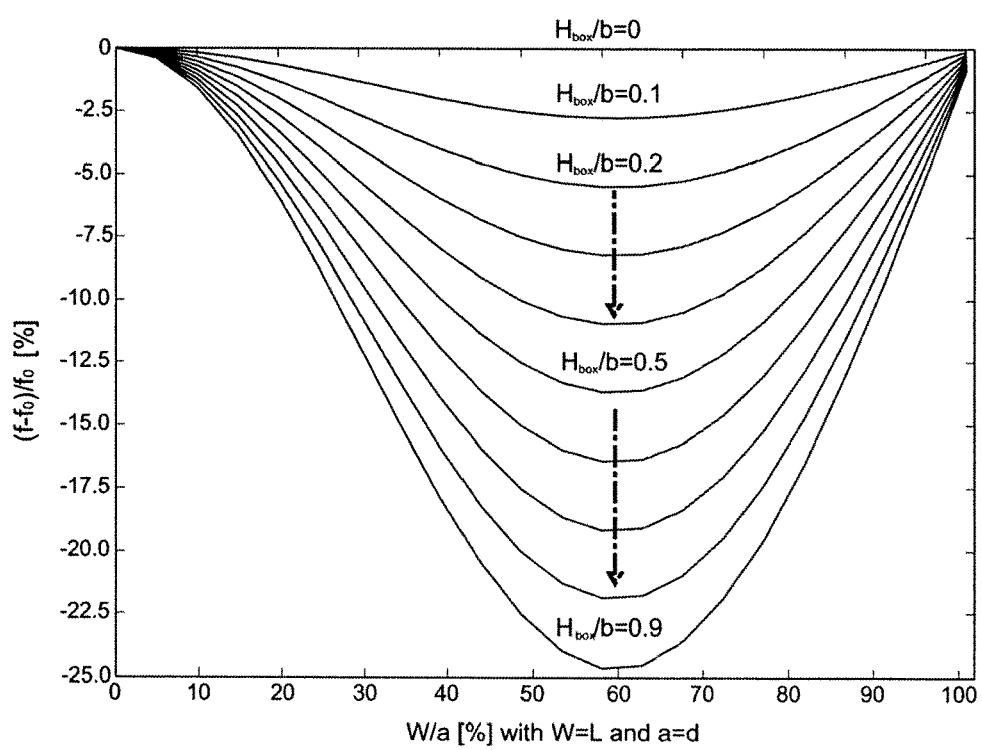

In FIG. 3 (a) an RF resonant cavity 13 of dimensions a×d×b is shown, having a centrally positioned tuning post 17 of dimensions W×L×$H_{box}$. The frequency shift $(f-f_0)/f_0$ is plotted as a function of the ratio of lateral dimensions of the cavity and post (horizontal axis: W/a in percents), and ratios of $H_{box}$ to b (from 0 to 0.9). The frequency shift is the highest for relatively tall tuning posts ($H_{box}$/b=0.9) having a ratio W/a close to 60%.

Figure 4:
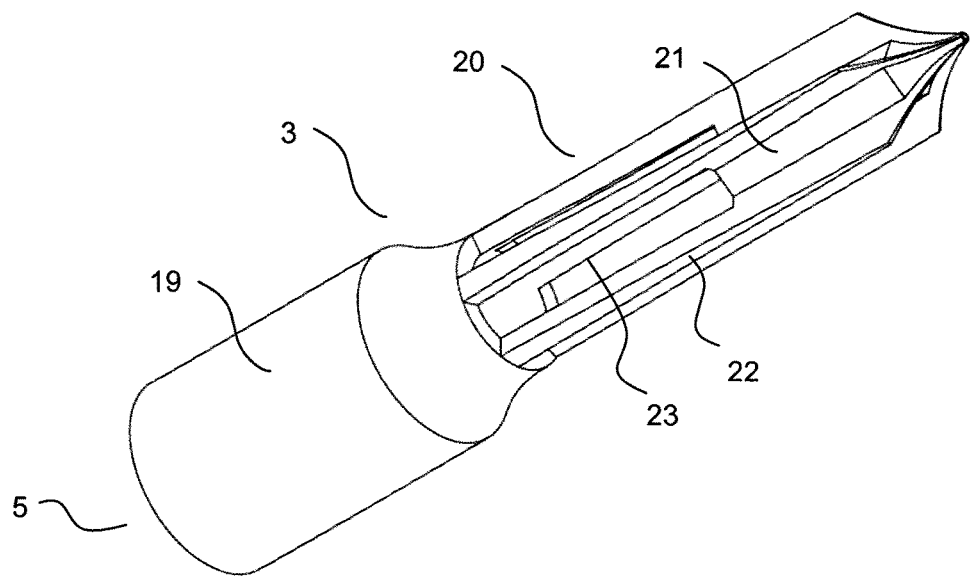
FIG. 4 shows a perspective view of a microneedle of the sensor.

An example of a microneedle 3 is shown in FIG. 4. The microneedle has an elongated shape with a base portion 19 and a tip portion 20. The base portion is cylindrical and forms a capillary bore 5. The tip portion comprises a cap 21 for shielding the capillary bore. The tip portion is supported in the base portion by a set of elongated elements 22 forming a plurality of openings 23 around the circumference of the microneedle. These elongated elements extend along the longitudinal direction of the microneedle and also functions as cutting elements for cutting the skin.

Figure 5:
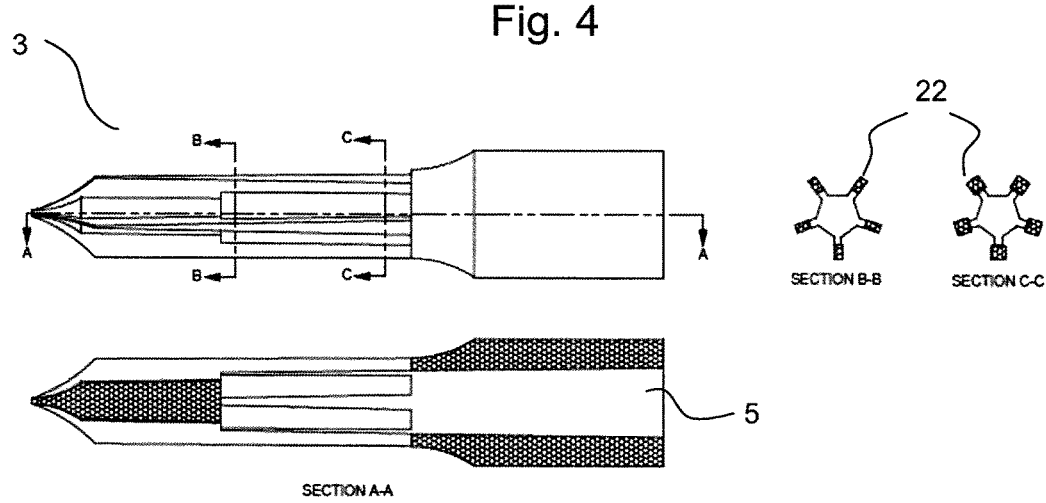
FIG. 5 shows various cross-sectional views of a microneedle of the sensor.

In FIG. 5 a microneedle 3 is shown in three different cross-sections A-A, B-B and C-C. In cross-section A-A the base portion is shown to form a capillary bore 5 for transporting fluid to the fluid cavity. The cap is supported by a plurality of elongated elements 22. In the example shown the number of elongated elements is 5, but the number of elongated elements may be in the range of 2-20. In sections B-B and C-C it is shown that the elongated elements are narrowed down towards the tip portion of the microneedle to form cutting elements for cutting the skin during penetration.

During operation of the sensor as shown in FIG. 1-2, the tip of a finger is pressed towards the microneedles 3 and supported by the ring-shaped frame structure 4. The skin is then stretched by the supporting structure, such that penetration of the microneedles through the skin is facilitated. The microneedles are penetrated into the skin by cutting the skin by means of the sharp tip portion of the needle, and by means of the elongated cutting elements. Bodily fluid in or underneath the skin of the finger is extracted by means of the plurality of openings of the microneedles. The bodily fluid may be e.g. blood or interstitial fluid. The bodily fluid is extracted by capillary suction forces into the capillary bore. The cap reduces the risk of the capillary bore of the microneedles are clogged by tissue material from the finger.

The sample of bodily fluid is thereafter transported to and collected in the fluid cavity, e.g. by capillary suction.

To analyze e.g. the glucose content of the bodily fluid, the perturbation of the cavity resonator is monitored. The glucose content will change the permittivity of the bodily fluid collected in the fluid cavity, which in turn will affect the resonance of the RF cavity resonator. The frequency response of the RF cavity resonator may thus be used for monitoring any change in the permittivity value in the bodily fluid. The changes that could be detected by the cavity resonator are a shift in the resonance frequency and/or a change in the bandwidth of the resonance of the cavity resonator. The permittivity accounts for the impedance that is encountered when forming an electric field in a medium. The response of the probing materials to external fields depends on the frequency of the field. This frequency dependence reflects the stored energy within the medium ($\varepsilon'$) and the dissipation (loss) of energy within the medium ($\varepsilon''$) and is represented by a complex function of the frequency (f) of the applied field.

$$\varepsilon(f)=\varepsilon_r'(f)+i\varepsilon_r''(f)$$

Figure 6:
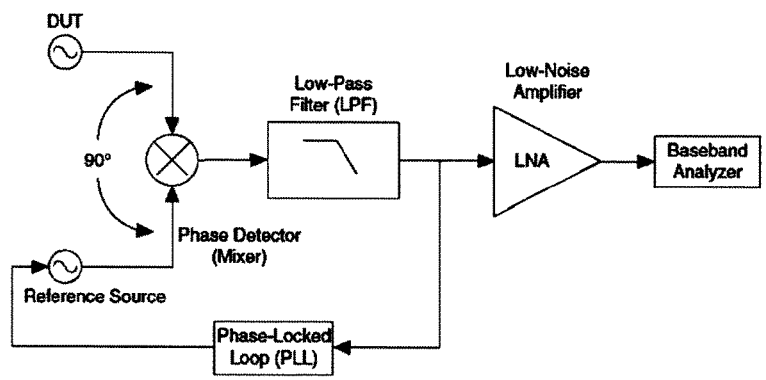
FIG. 6 shows an electronic read-out circuit for the sensor.

The resonance of a cavity resonator is highly selective in frequency, related to the quality factor of the resonator. The impact of probing different dielectrics in the fluid cavity results in a shift of the resonance frequency and a change in the bandwidth of the resonance, as follows:

$$\varepsilon_r' = \frac{V_c(f_c - f_s)}{2V_s f_s} \text{ and } \varepsilon_r'' = \frac{V_c}{4V_s}\left(\frac{1}{Q_s} - \frac{1}{Q_c}\right)$$

where, the permittivity is described by $\varepsilon_r'$ and $\varepsilon_r''$, the latest being related to the dissipation (loss) of energy within the medium; $V_c$ and $V_s$ the cavity and sample volume, respectively: $f_c$ and $f_s$ the resonance frequency and $Q_c$ and $Q_s$ the quality factor, without and with perturbation, respectively. In FIG. 6, a basic block diagram of an electronic read-out circuit for the sensor is disclosed. The read-out circuit converts the high frequencies used for dielectric characterization into baseband signals and both information on the resonant frequency and quality factor may be retrieved. A phase noise measurement technique could be devised to measure the frequency of oscillation and the phase noise of the oscillator. The frequency of oscillation is then directly related to the resonant frequency and the phase-noise of the oscillator to the Q-factor of the cavity resonator.

A low phase noise oscillator comprises a negative resistance circuit module, a cavity resonator and the coupling between the resonant cavity and the negative resistance (DUT in FIG. 6). Two embodiments for the oscillator are possible. The first one is a reflection type oscillator. It is composed of one port resonator connected to a negative resistance circuit. The second one is a thru-type oscillator, wherein the resonator acts like a filter through the feedback loop of an active circuit.

Among the phase-noise measurement techniques, the "Reference Source/PLL Method" could be implemented in an embedded circuit. FIG. 6 shows a schematic circuit for the phase detection method using reference source/PLL techniques. The basis of this method is to use a PLL in conjunction with a double balanced mixer (DBM) used for the Phase Detection (PD).

When the phase difference is set to 90° (quadrature) the voltage output after the Low-Pass-Filter (LPF) will be zero volts. In case of small phase angles the LPF output is simplified into a voltage proportional to the phase difference of the two input signals, at the output of the detector. This allows measuring the phase noise mixed down to the baseband with a conversion loss. Any phase fluctuation from quadrature will result in a voltage fluctuation at the output. Several methods have been developed based upon the phase detector concept. Among them, the reference source/PLL (phase-locked-loop) is one of the most widely used methods. The phase noise is directly proportional to the Q factor, following Lesson's equation $L(\Delta\omega)$:

$$L(\Delta\omega) = 10\log\left\{\frac{2FkT}{P_{sig}} \cdot \left[1 + \left(\frac{\omega_0}{2Q\Delta\omega}\right)^2\right] \cdot \left(1 + \frac{\Delta\omega_{1/f^3}}{|\Delta\omega|}\right)\right\}$$

where F is an empirical parameter (often called the "device excess noise number"), k is Boltzman's constant. T is the absolute temperature, $P_{sig}$ is the average power dissipated, $\omega_0$ is the oscillation frequency, Q is the loaded quality factor, $\Delta\omega$ is the offset from the carrier and $\Delta\omega_{1/f^3}$ is the frequency of the corner between $1/f^3$ and $1/f^2$ region.

The voltage resulting of the mixing between a pair of oscillator i.e. the sensing oscillator and a reference oscillator could be used for the sensing oscillator's frequency read-out and will subsequently provide an information on the resonant frequency and $\varepsilon_r'$. This is heterodyne frequency measurement method. The voltage fluctuations are fed to a voltage to frequency converter which in turn feeds a frequency counter to read out the frequency fluctuations. The second reference oscillator could be a PLL synthesized oscillator based on a second integrated cavity resonator, fixed in frequency.

The signal of a voltage controlled source (VCO) is down mixed with the signal of the sensing oscillator. The mixing output is connected through a low pass filter to a phase lock amplifier (PLL). The noise output is typically sent to a low noise amplifier followed by an audio spectrum analyzer, a baseband analyzer. This may be used for the phase-noise measurement and will subsequently provide the information on the Q-factor and $\varepsilon_r''$.

Figure 7:
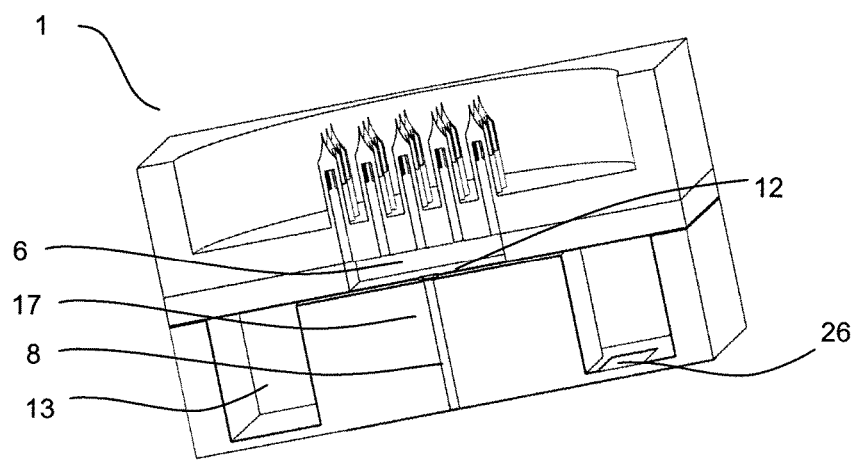
FIG. 7 shows a microfabricated sensor according to a second example, in a cross-sectional view.

Another embodiment of the sensor 1 is shown in FIG. 7. The sensor differs from what is previously disclosed in that the RF resonant cavity 13 is coupled to the fluid cavity 6 through a small perturbation chamber 24 extending into the RF resonant cavity. The perturbation chamber is separated from the RF resonant cavity by means of separating walls 25 connecting the membrane 12 and the tuning post 17. These separating walls are not metalized, and they are dimensioned such that the RF energy is coupled into the fluid in the perturbation chamber with limited influence from the material of the separating walls. The perturbation chamber is connected to the fluid exit port 8 which extends through the tuning post. Another feature is that, since the electromagnetic waves are couple into the fluid cavity through the perturbation chamber, the dimensions of the fluid cavity 6 functioning as a fluid reservoir connected to the microneedles may be made more shallow. Also in the figure, a coupling slot 26 for coupling electromagnetic energy into and out from the RF resonant cavity is provided. The sensor as shown in FIGS. 1 and 2 may be provided with similar coupling slots.

Figure 8:
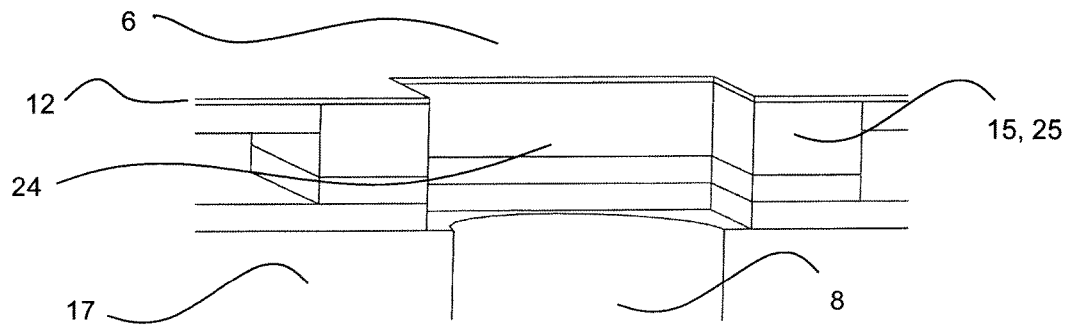
FIG. 8 shows a close-up of a portion of a microfabricated sensor according to the second example.

In FIG. 8 the construction of the perturbation chamber is shown in more detail. Between the fluid cavity 6, delimited by the membrane 12, and the tuning post 17, a portion 24 of the fluid cavity 6 extends into the RF resonant cavity by bridging the gap between the membrane and the tuning post. This portion of the fluid chamber is surrounded by a square shaped structure of separating walls 15, 25. Thereby a perturbation chamber 24 is formed by the separating walls 15, 25. The walls are configured such that the RF waves in the RF resonant cavity extend into the fluid present in the perturbation chamber. This means e.g. that they are made of a dielectric material, and of dimensioned to be thin to minimize any influence on the electromagnetic fields. Another advantage of this structure is that it will support the membrane, thus forming a more robust construction.

In the following, a method of microfabricating a sensor is described as means of explanation. Microfabrication is defined to include fabrication techniques of structures in the micrometer range. The final components may be in the order of millimeters, or even centimeters, including feature sizes down to sub-micrometers. Micromachining may include one or more of lithography, wet etching, dry etching (such as deep reactive ion etching, DRIE) etc, but may further include one or more of electron or ion bean machining, plasma beam machining, laser machining, electro discharge machining, micromilling, micromolding, microreplication in a polymer, micro solid freeform fabrication, micro stereo lithography, electroplating and the like process steps and methods. Micromachining allows for a miniaturised sensor device that may be batch fabricated and thus produced at a reduced cost.

The lithographic steps of the method of microfabricating the sensor are performed similarly. The first step in the lithography is to prime the wafers in a HMDS oven. This gives a better adhesion for the resist, which is later coated on the wafer. As a side effect, the wafer will also be hydrophobic.

The next step in the lithography is the resist coating, such as with a positive resist.

The following step in the lithography is to create the pattern on the wafer, so the etching pattern may be created later. A mask for the different etching structures and the wafer is exposed with UV light creating a pattern in the resist. The resist (with the pattern) works as a mask during the etching, this allows the wafer to be etched and only the wanted pattern is created and the resist protect the rest of the surface.

The pattern of the resist is thereafter developed and hard baked. The purpose of hard baking is to remove residual solvent and to improve the adhesion of the resist so it will protect the wafer enough.

After silicon etching, a resist stripping step is carried out to remove the resist and to access the next mask. This is advantageous, since one mask may be removed and another silicon etching may be carried out with an oxide mask that is covered by the previous resist mask.

Oxide stripping is done by dipping the wafer in 50% HF and is done to remove the oxide layer. When forming the needles, oxidation and oxide stripping may be repeated until a sharp enough tip of the needle is created.

The oxide etchings are carried out to create an oxide mask, since a resist mask may not be done after a first silicon etching. Therefore, the second etch patterns is created by resist followed by oxide etch before the first etch pattern is created by resist. An oxide etch is also carried out to remove the oxide from the wafer, were the silicon etch needs to take place afterwards.

In fabricating the sensors, three wafers are processed and later on bonded together;

- A needle wafer (NW) e.g. in the form of a Double-side polished (DSP) Silicon wafer for microneedles and bore holes. The wafer may e.g. be 4" of (100)-oriented silicon, p-doped, 1-10 Ωcm or eq. normal resistivity, with a thickness of 500-1000±25 μm.
- A fluid wafer (FW) e.g. in the form of a Double-side polished (DSP) 4" Silicon, of (100)-oriented silicon, p-doped, 1-10 Ωcm or eq. normal resistivity, with a thickness of 300±15 μm.
- An RF cavity wafer (CW) e.g. in the form of a Silicon-On-Insulator (SOI) wafer having a 15 μm thick device layer, and preferably in high resistivity silicon.

The wafers are single crystalline silicon wafers, but other materials such as glass, metal and plastics are also conceivable to be used in the sensor. The processing of the sensor comprises the steps of

- Patterning and etching of needle wafer (NW) with bore holes through the wafer and microneedles,
- Patterning and etching of fluid wafer (FW),
- Patterning and etching of RF cavity wafer (CW),
- Bonding (e.g. direct bonding) of needle wafer and fluid wafer,
- Metallization of fluid and RF cavity wafer,
- Bonding (e.g. thermocompression bonding) between needle/fluid and cavity wafers, and
- Dicing the wafer stack into individual components.

Figure 9:
FIG. 9 outlines the process steps to microfabricate a microneedle wafer for a sensor as disclosed herein.
Figure 9:
Figure 9:
Figure 9:
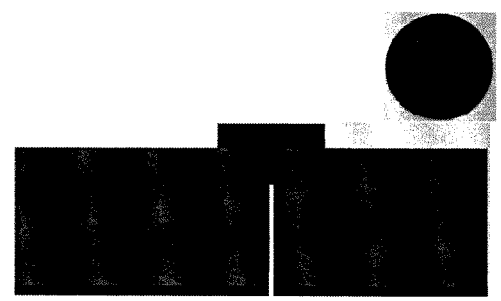
Figure 9:
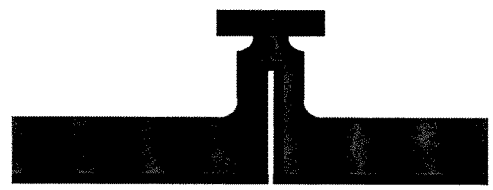
Figure 9:
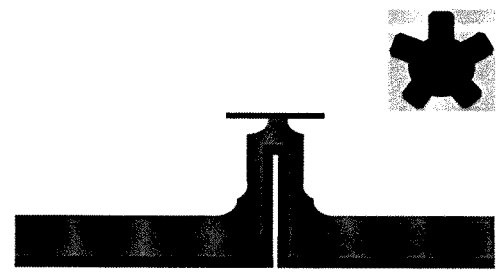
Figure 9:
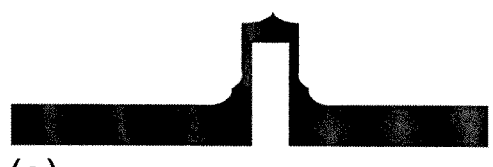

The structures are etched in an Inductively Coupled Plasma (ICP) Deep Reactive Ion Etching (DRIE) apparatus. In FIG. 9 the process steps of fabricating a microneedle wafer are shown.

The wafer is provided with a layer of thermal oxide, which is patterned by lithography (a) in order to etch the bores of the microneedles with DRIE (b). The structure is thereafter stripped and oxidized again (c). The oxide on the top side is patterned (star shape), and a second resist mask (circular) is deposited and patterned (d). The microneedles are etched by a combination of isotropic and anisotropic etching, with the circular mask (e). Thereafter the star mask is exposed by removing the resist mask, and the needles are etched by an anisotropic etch (f). The oxide is thereafter stripped and the microneedles are exposed, possibly followed by a further oxidation and stripping step to sharpen the tips of the needles.

Figure 10:
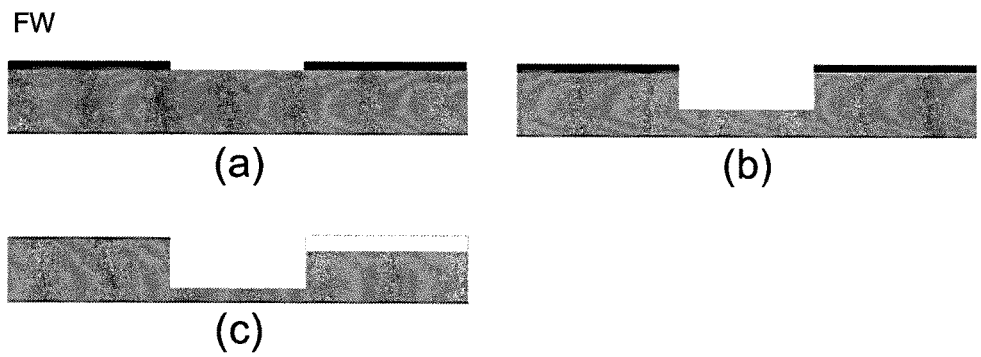
FIG. 10 outlines the process steps to microfabricate a fluid cavity wafer according to the first example.

FIG. 10 shows one example of processing the fluid cavity wafer (FW), according to the first example of a sensor as described in relation to FIGS. 1 and 2. The silicon wafer is provided with an oxide and resist mask by lithography as described above (a). The fluid cavity is thereafter etched by DRIE (b), and the second mask (fluid exit port) is exposed. The fluid exit port is etched (c) and the oxide is stripped.

Figure 11:
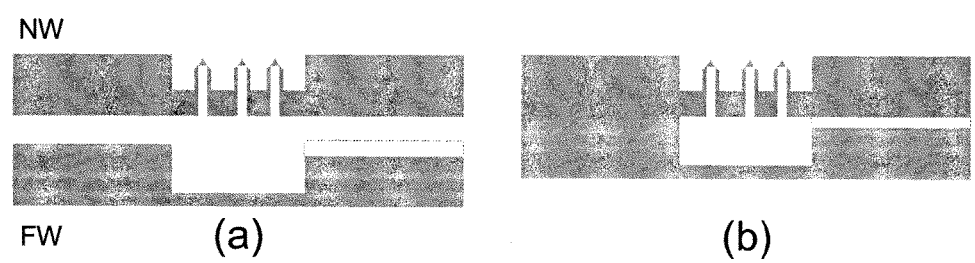
FIG. 11 outlines the process steps to bond a microneedle wafer and a fluid cavity wafer.

As shown in FIG. 11, the needle wafer (NW) and the fluid cavity wafer (CW) are aligned (a) and bonded (b) by direct bonding of the silicon wafers.

Figure 12:
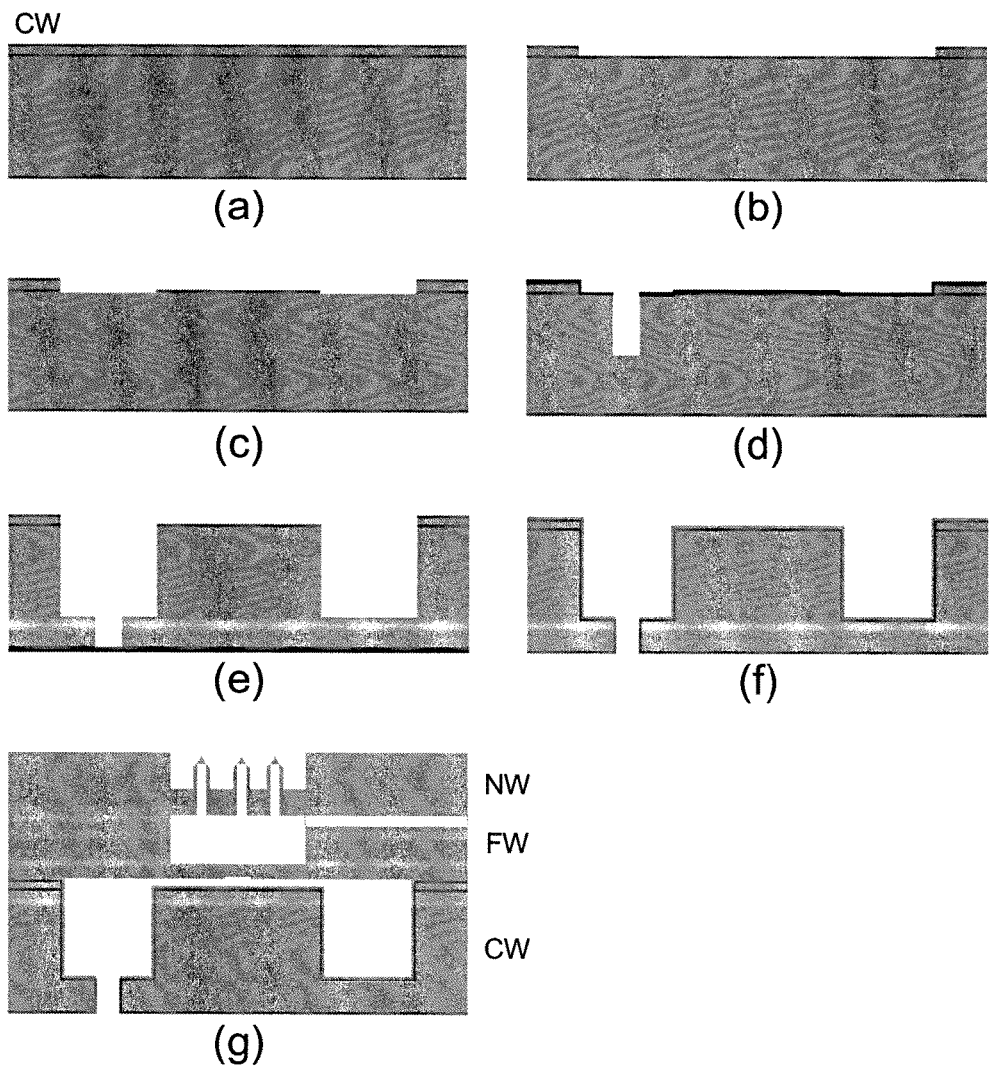
FIG. 12 outlines the process steps to microfabricate a RF resonant cavity wafer, and a cross-section of the resulting sensor, according to the first example.

The RF resonant cavity wafer (CW) is processed as shown in FIG. 12, according to the first example of a sensor as described herein. A SOI wafer is oxidized by thermal oxidation (a). The device layer of the SOI wafer is etched down to the buried oxide layer (b). The oxide is patterned to form an oxide mask (c) and a resist mask is deposited and patterned followed by etching of the coupling slot (d). Thereafter the resist mask is stripped and the RF resonant cavity is etched, leaving the tuning post (e). A bottom metallization is removed and the structure is oxidized and a layer of metal is deposited on the cavity walls by means of sputtering or evaporation (f). A thicker layer of metallization may be obtained by electroplating. Also the bottom side of the bonded needle/fluid wafer stack is metalized. The wafer stack and the RF resonant cavity wafer are thereafter assembled by thermo-compression bonding under elevated temperature (e.g. 400° C.) and pressure (g). Individual sensor elements are diced from the bonded wafer stack by means of a dicing saw.

Figure 13:
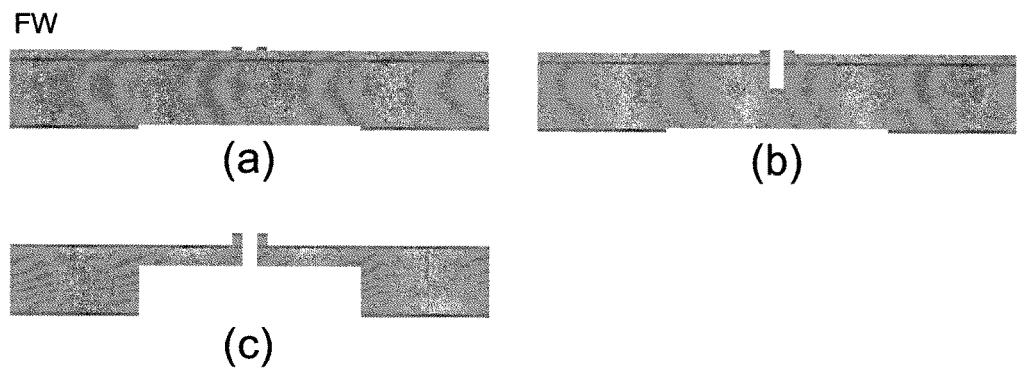
FIG. 13 outlines the process steps to microfabricate a fluid cavity wafer according to the second example.

According to a second example of a sensor, as described in relation to FIGS. 7 and 8, the fluid wafer (FW) is processed from a SOI wafer as shown in FIG. 13. The wafer is oxidized and the oxide layer is patterned on both sides to define masks for the fluid cavity and for the perturbation chamber (a). A resist mask is deposited and patterned for etching of a through hole from the fluid cavity to the perturbation chamber (b). Thereafter the fluid cavity and perturbation chamber are etched by using the oxide masks (c). The side of the wafer facing the RF cavity wafer is metalized.

Figure 14:
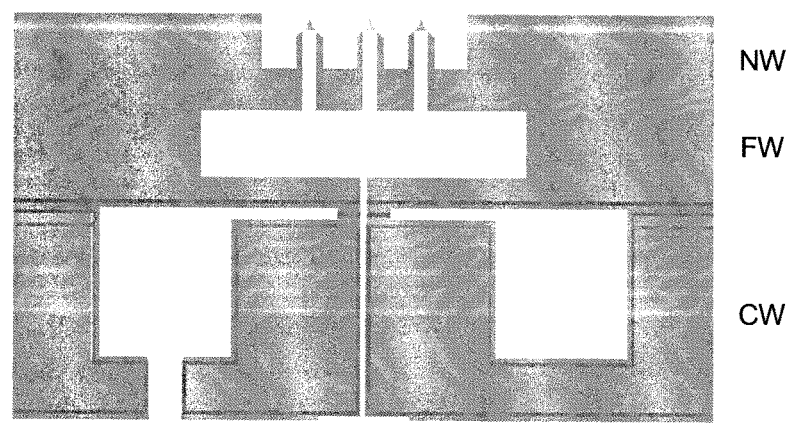
FIG. 14 shows a cross-section of the resulting sensor according to the second example.

The RF cavity wafer (CW) is processed similarly to what is described above in relation to FIG. 12, with the addition of etching the fluid exit port through the tuning post. The wafers are bonded by means of thermo-compression bonding and diced into individual sensor components. The resulting device is shown in FIG. 14.

The sensor with the RF resonant cavity could be mounted on a carrier by which means the RF cavity is sealed. The carrier may comprise suitable RF transmission lines for injection of electromagnetic energy into the RF cavity through the coupling slot. Sensing may be performed by either the same transmission line (reflection mode) or another additional coupling slot (transmission mode).

The invention claimed is:

1. A microfabricated sensor (1) for detecting a component in bodily fluid, comprising: an inlet lens (2) for receiving a sample of the bodily fluid, a fluid cavity (6) connected to the inlet means for receiving the sample of bodily fluid from the inlet means, a radio frequency (RF) resonant cavity (13), delimited by walls (14), wherein at least one of the walls forms a separating wall (15), separating the fluid cavity from the RF resonant cavity, wherein the separating wall comprises a membrane (12) and is configured such that dielectric properties of the bodily fluid in the fluid cavity provide an influence on electromagnetic properties of the RF resonant cavity.

2. The microfabricated sensor according to claim 1, wherein the walls (14) of the RF resonant cavity are at least partly metallized, but wherein an RF coupling region (16) is provided at the separating wall, such that to couple the RF resonant cavity to the fluid cavity.

3. The microfabricated sensor according to claim 2, wherein the RF coupling region (16) is a non-metallised area of the separated wall.

4. The microfabricated sensor according to claim 1, wherein the fluid cavity (6) comprises a portion (24) extending into the RF resonant cavity, and wherein the separating wall (15) comprises a wall (25) delimiting the portion of the fluid cavity.

5. The microfabricated sensor according to claim 1, wherein the RF resonant cavity comprises a tuning post (17) or a plurality of tuning posts.

6. The microfabricated sensor according to claim 5 wherein the tuning post (17), or the plurality of tuning posts, is configured to provide a gap (18) in the RF resonant cavity, in the vicinity of the separating wall (15).

7. The microfabricated sensor according to claim 6, wherein the fluid cavity (6) comprises a portion (24) extending into the RF resonant cavity, which portion (24) extends over the gap (18) within the RF resonant cavity.

8. The microfabricated sensor according to claim 1, wherein the microfabricated sensor comprises a fluid exit port (8) connected to the fluid cavity (6) for drainage of fluid from the fluid cavity.

9. The microfabricated sensor according to claim 7, wherein the microfabricated sensor comprises a fluid exit port (8) connected to the fluid cavity (6) for drainage of fluid from the fluid cavity, which fluid exit port (8) extends through the tuning post (17).

10. The microfabricated sensor according to claim 1 provided with at least one or more RF coupling slots (26).

11. The microfabricated sensor according to claim 1, wherein the RF resonant cavity (13) is sealed off from the fluid cavity (6).

12. The microfabricated sensor according to claim 1, wherein the inlet means comprises at least one hollow microneedle (3) for extraction of the sample of bodily fluid, preferably a plurality of hollow microneedles (3), more preferably 10 to 100 microneedles.

13. The microfabricated sensor according to claim 12, wherein the at least one microneedle is at least partly surrounded by a frame structure (4) dimensioned to support the tip of a finger.

14. The microfabricated sensor according to claim 13, wherein the frame structure (4) dimensioned to support the tip of a finger is a ring shaped structure protruding along the longitudinal direction of the at least one microneedle, and preferably having a diameter of 1-5 mm, more preferably 2-3 mm.

15. The microfabricated sensor according to claim 1, therein the microfabricated sensor is configured for detecting a level of glucose in the bodily fluid.

16. A method of detecting a component in bodily fluid comprising: providing a microfabricated sensor according to claim 1, providing the sample of bodily fluid at the inlet means, receiving the fluid sample in the fluid cavity, performing an RF measurement by exciting the RF resonant cavity with an RF signal and detecting an RF response, and detecting the component based on the performed RF measurement.

17. The method according to claim 16, wherein the detection of the component is based on an oscillator circuit using a one or two port coupling structure into the RF cavity resonator.

18. The method according to claim 16, wherein detecting the component comprises determining the level of the component based on the performed RF measurement.

19. The method according to claim 16, wherein the component is detected by measuring a shift in resonance frequency or a change in bandwidth or amplitude of the resonance.

20. The method according to claim 16, wherein the bodily fluid is blood and/or interstitial fluid.

21. The method according to claim 16, wherein the component is glucose.

* * * * *